United States Patent
Kim et al.

(10) Patent No.: US 10,020,453 B2
(45) Date of Patent: Jul. 10, 2018

(54) ORGANIC LIGHT EMITTING DISPLAY DEVICE

(71) Applicant: LG Display Co., Ltd., Seoul (KR)

(72) Inventors: DoHan Kim, Gyeonggi-do (KR); JungKeun Kim, Seoul (KR); Hyeseung Kang, Seoul (KR); Min Yun, Gyeonggi-do (KR); SeungHee Yoon, Seoul (KR)

(73) Assignee: LG Display Co., Ltd., Seoul (KR)

( * ) Notice: Subject to any disclaimer, the term of this patent is extended or adjusted under 35 U.S.C. 154(b) by 421 days.

(21) Appl. No.: 14/849,804

(22) Filed: Sep. 10, 2015

(65) Prior Publication Data

US 2016/0149142 A1    May 26, 2016

(30) Foreign Application Priority Data

Nov. 26, 2014 (KR) .................. 10-2014-0166487

(51) Int. Cl.
*H01L 51/50* (2006.01)
*H01L 51/00* (2006.01)
*C07D 487/06* (2006.01)
*C09K 11/02* (2006.01)

(52) U.S. Cl.
CPC ........ *H01L 51/0072* (2013.01); *C07D 487/06* (2013.01); *C09K 11/025* (2013.01); *H01L 51/0074* (2013.01); *H01L 51/5016* (2013.01)

(58) Field of Classification Search
None
See application file for complete search history.

(56) References Cited

U.S. PATENT DOCUMENTS

| 2012/0075273 A1* | 3/2012 | Abe ..................... C07D 487/06 345/205 |
| 2012/0292576 A1* | 11/2012 | Parham ................ C07D 209/86 252/500 |
| 2013/0320310 A1 | 12/2013 | Yamamoto et al. |
| 2015/0179955 A1* | 6/2015 | Miyata ................ H01L 51/0072 257/40 |

FOREIGN PATENT DOCUMENTS

| CN | 102725268 A | 10/2012 |
| CN | 104974166 A | 10/2015 |
| EP | 2 927 234 A1 | 10/2015 |
| WO | 2012/015017 A1 | 2/2012 |

OTHER PUBLICATIONS

Extended European Search Report dated Jan. 18, 2016 by the European Patent Office in corresponding European Patent Application No. 15182932.2.
First Office Action issued in corresponding Chinese Patent Application No. 201510580558.6 dated Jun. 14, 2017.

* cited by examiner

*Primary Examiner* — Gregory D Clark
(74) *Attorney, Agent, or Firm* — Morgan, Lewis & Bockius LLP

(57) ABSTRACT

An organic light emitting display device and an organic layer are disclosed. The organic light emitting display device includes an anode, an organic layer over the anode, and a cathode over the organic layer. In one aspect, the organic layer may include an indolocarbazole compound. In another aspect, the organic layer may include a compound by linking a carbazole derivative and a carbazole compound to an aryl group or a heteroaryl group.

7 Claims, 2 Drawing Sheets

ORGANIC LIGHT EMITTING DISPLAY DEVICE

This application claims the priority benefit of Korean Patent Application No. 10-2014-0166487 filed on Nov. 26, 2014, which is incorporated herein by reference for all purposes as if fully set forth herein.

BACKGROUND

Field of the Invention

The present invention relates to an indolocarbazole compound and an organic light emitting display device comprising the same, and more particularly, to an indolocarbazole compound which is capable of reducing the operating voltage of an organic light emitting display device and improving its efficiency and lifetime and an organic light emitting display device comprising the same.

Discussion of the Related Art

With the development of multimedia, flat panel displays (FDPs) are becoming more and more important. Accordingly, a variety of panel displays such as liquid crystal display (LCDs), plasma display panels (PDPs), field emission displays (FEDs), organic light emitting display devices, and the like are put to practical use.

Among them, the organic light emitting display devices are advantageous in that they can be formed on a flexible transparent substrate, such as plastic, can be driven at a low voltage of 10 V or less, have relatively low power consumption, and excellent color sensitivity, as compared to a plasma display panel or inorganic light emitting display. Further, the organic light emitting display device can represent three colors of red, green and blue, and thus is drawing a great deal of attention as a next-generation full-color display device.

An organic light emitting display device can be formed by sequentially stacking an anode, a hole injection layer, a hole transport layer, a light emitting layer, and electron transport layer, an electron injection layer, and a cathode. For a luminescent material, excitons are formed by the recombination of electrons and holes injected from the two electrodes. Singlet excitons and triplet excitons are involved in fluorescence and phosphorescence, respectively. In recent years, there is a growing trend that phosphorescent materials are replacing fluorescent materials. For a fluorescent material, singlet excitons, which produce only 25% of all excitons formed in the light emitting layer, are used to produce light, and triplet excitons, which produce 75% of the excitons, are mostly lost and transformed into heat. Phosphorescent materials, in contrast, have a light emission mechanism for converting both singlet and triplet excitons into light.

A light emitting process of a phosphorescent material will be discussed briefly. Holes injected from the anode and electrons injected from the cathode meet in a host material of the emission layer. Though a hole and an electron may be paired in a dopant in some cases, a large amount of holes and electrons meet in the host in most cases due to high concentration of the host. At this point, the singlet excitons formed in the host transfer energy to the singlets or triplets of the dopant, while the triplet excitons transfer energy to the triplets of the dopant.

Since the excitons transferred to the singlets of the dopant are transferred to the triplets of the dopant by intersystem crossing, the first destination of all the excitons is a triplet level of the dopant. The thus-formed excitons are transferred to the ground state, and emit light. If the triplet energy of the hole transport layer or electron transport layer adjacent to the front and back of the light emitting layer is less than the triplet energy of the dopant, backward energy transfer takes place from the dopant or host to these layers, and this leads to an abrupt decrease in efficiency. Accordingly, the triplet energy of the hole/electron transport layers, as well as the host material of the light emitting layer, plays a very important role in phosphorescent devices.

For efficient energy transfer from the host to the dopant, the triplet energy of the host must be greater than the triplet energy of the dopant. However, materials with high triplet energy cause deteriorations of the device, including a decrease in device efficiency and a voltage rise. Materials with low thermal stability and low electric stability can decrease the device lifetime. Accordingly, there is an urgent need for the development of novel phosphorescent materials with superior thermal stability and superior electric stability.

SUMMARY

Accordingly, the present invention is directed to an organic light emitting display device that substantially obviates one or more of the problems due to limitations and disadvantages of the related art.

An object of the present invention is to provide an indolocarbazole compound which is capable of reducing the operating voltage of an organic light emitting display device and improving its efficiency and lifetime and an organic light emitting display device comprising the same.

Additional features and advantages of the invention will be set forth in the descriptions which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the invention, as embodied and broadly described, an organic light emitting display device comprises an anode, an organic layer over the anode, and a cathode over the organic layer, wherein the organic layer includes an indolocarbazole compound may be represented by the following Chemical Formula 1:

[Chemical Formula 1]

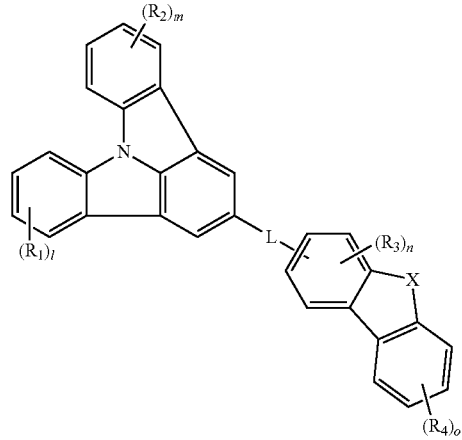

where X is one among N, O, S, and Se, wherein N is bound to one among H, a halogen atom, a cyano group, a substituted or unsubstituted alkyl group having 1 to 20 carbon atoms, a substituted or unsubstituted aryl group having 6 to 30 carbon atoms, a substituted or unsubstituted heteroaryl group having 2 to 30 carbon atoms, a substituted or unsubstituted aryl amino group having 6 to 30 carbon atoms, and a substituted or unsubstituted heteroaryl amino group having 2 to 30 carbon atoms, $R_1$ to $R_4$ are independently one among H, a halogen atom, a cyano group, a substituted or unsubstituted alkyl group having 1 to 20 carbon atoms, a substituted or unsubstituted aryl group having 6 to 30 carbon atoms, a substituted or unsubstituted heteroaryl group having 2 to 30 carbon atoms, a substituted or unsubstituted aryl amino group having 6 to 30 carbon atoms, and a substituted or unsubstituted heteroaryl amino group having 2 to 30 carbon atoms, l, m, n, and o are an integer between 0 and 4, wherein, if any of l, m, n, and o has a value of 2 or more, the corresponding R is the same with each other or if any of l, m, n, and o has a value of 2 or more, the corresponding R is different from each other, and L is a substituted or unsubstituted aryl group having 6 to 30 carbon atoms or a substituted or unsubstituted heteroaryl group having 2 to 30 carbon atoms.

The indolocarbazole compound includes one among the following compounds:

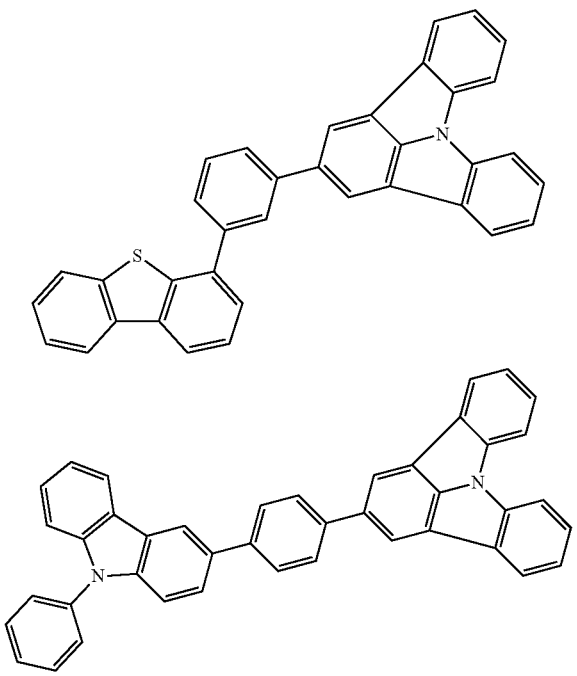

The organic layer includes a light emitting layer.

The indolocarbazole compound includes a host of the light emitting layer.

The organic layer comprises at least one among a hole transport layer, an electron blocking layer, a hole blocking layer, and an electron transport layer, and the at least one among a hole transport layer, an electron blocking layer, a hole blocking layer, and an electron transport layer includes the indolocarbazole compound.

In another aspect, an organic light emitting display device comprises an organic layer over an anode, and a cathode over the organic layer, wherein the organic layer includes a compound by linking a carbazole derivative and a carbazole compound to an aryl group or a heteroaryl group.

The organic layer includes a light emitting layer.

The organic layer includes a host for the light emitting layer.

The carbazole derivative and the carbazole compound have hole transfer properties, and the aryl group or the heteroaryl group has electron transfer properties.

An organic light emitting display device having the compound has reduced an operating voltage and increased efficiency and lifetime, as compared with an organic light emitting display without the compound.

The organic layer comprises at least one among a hole transport layer, an electron blocking layer, a hole blocking layer, and an electron transport layer, and at least one among a hole transport layer, an electron blocking layer, a hole blocking layer, and an electron transport layer includes the compound.

The compound includes a compound represented by the following Chemical Formula 1:

[Chemical Formula 1]

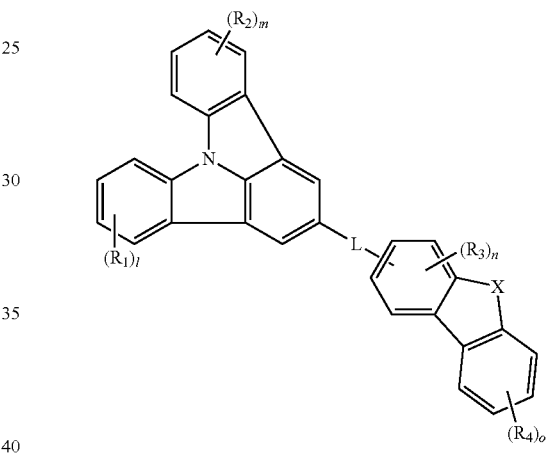

where X is one among N, O, S, and Se, wherein N is bound to one among H, a halogen atom, a cyano group, a substituted or unsubstituted alkyl group having 1 to 20 carbon atoms, a substituted or unsubstituted aryl group having 6 to 30 carbon atoms, a substituted or unsubstituted heteroaryl group having 2 to 30 carbon atoms, a substituted or unsubstituted aryl amino group having 6 to 30 carbon atoms, and a substituted or unsubstituted heteroaryl amino group having 2 to 30 carbon atoms, $R_1$ to $R_4$ are independently one among H, a halogen atom, a cyano group, a substituted or unsubstituted alkyl group having 1 to 20 carbon atoms, a substituted or unsubstituted aryl group having 6 to 30 carbon atoms, a substituted or unsubstituted heteroaryl group having 2 to 30 carbon atoms, a substituted or unsubstituted aryl amino group having 6 to 30 carbon atoms, and a substituted or unsubstituted heteroaryl amino group having 2 to 30 carbon atoms, l, m, n, and o are an integer between 0 and 4, wherein, if any of l, m, n, and o has a value of 2 or more, the corresponding R is the same with each other or if any of l, m, n, and o has a value of 2 or more, the corresponding R is different from each other, and L is a substituted or unsubstituted aryl group having 6 to 30 carbon atoms or a substituted or unsubstituted heteroaryl group having 2 to 30 carbon atoms.

The compound includes one among the following compounds:

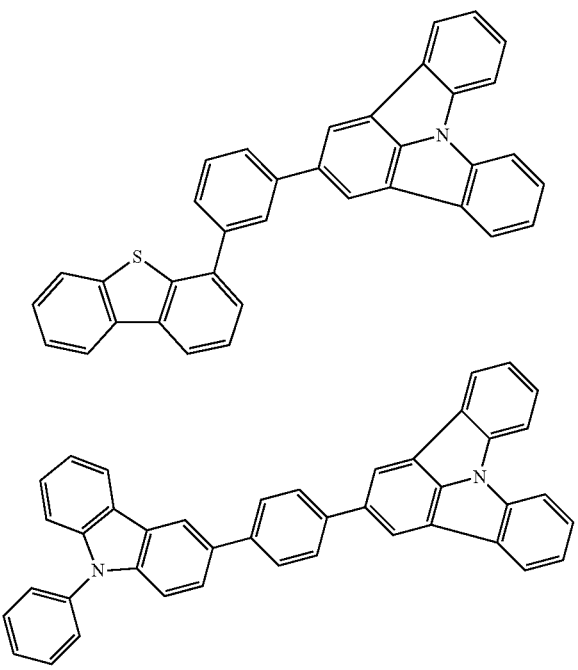

In another aspect, an organic layer comprises a host material with an indolocarbazole compound bound to a compound having an aryl group or a heteroaryl group to optimize a lifetime and an efficiency of an organic emissive layer.

The organic layer includes a compound represented by the following Chemical Formula 1:

[Chemical Formula 1]

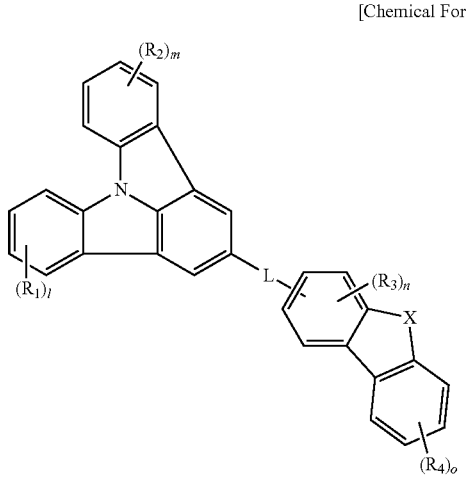

where X is one among N, O, S, and Se, wherein N is bound to one among H, a halogen atom, a cyano group, a substituted or unsubstituted alkyl group having 1 to 20 carbon atoms, a substituted or unsubstituted aryl group having 6 to 30 carbon atoms, a substituted or unsubstituted heteroaryl group having 2 to 30 carbon atoms, a substituted or unsubstituted aryl amino group having 6 to 30 carbon atoms, and a substituted or unsubstituted heteroaryl amino group having 2 to 30 carbon atoms, $R_1$ to $R_4$ are independently one among H, heavy hydrogen, a halogen atom, a cyano group, a substituted or unsubstituted alkyl group having 1 to 20 carbon atoms, a substituted or unsubstituted aryl group having 6 to 30 carbon atoms, a substituted or unsubstituted heteroaryl group having 2 to 30 carbon atoms, a substituted or unsubstituted aryl amino group having 6 to carbon atoms, and a substituted or unsubstituted heteroaryl amino group having 2 to 30 carbon atoms, l, m, n, and o are an integer between 0 and 4, wherein, if any of l, m, n, and o has a value of 2 or more, the corresponding R is the same with each other or if any of l, m, n, and o has a value of 2 or more, the corresponding R is different from each other, and L is a substituted or unsubstituted aryl group having 6 to 30 carbon atoms or a substituted or unsubstituted heteroaryl group having 2 to 30 carbon atoms.

The compound includes one among the following compounds:

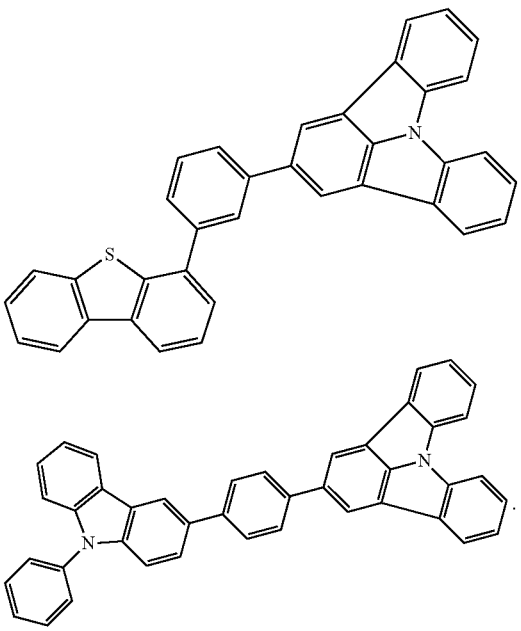

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION

Figure 1:
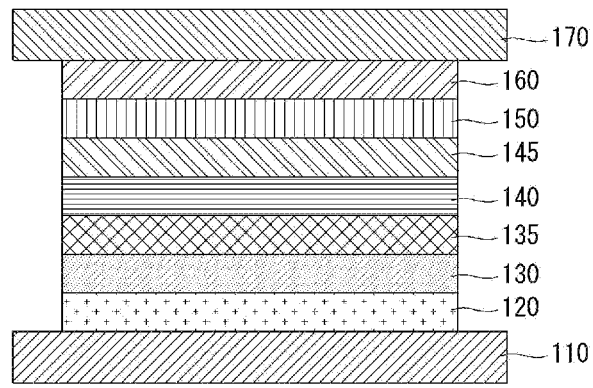
FIG. 1 is a view showing an organic light emitting display device according to an example embodiment of the present invention.

The advantages and features of the present invention and methods for accomplishing the same may be understood more readily by reference to the following detailed descriptions of exemplary embodiments and the accompanying drawings. The present invention may, however, be embodied in many different forms and should not be construed as being limited to the exemplary embodiments set forth herein. Rather, these exemplary embodiments are provided so that this disclosure will be thorough and complete and will fully convey the concept of the present invention to those skilled in the art, and the present invention is defined by the appended claims The shapes, sizes, percentages, angles, numbers, etc shown in the figures to describe the exemplary embodiments of the present invention are merely examples and not limited to those shown in the figures. Like reference numerals denote like elements throughout the specification. In describing the present invention, detailed descriptions of related well-known technologies will be omitted to avoid unnecessary obscuring the present invention. When the terms 'comprise', 'have', 'consist of' and the like are used, other parts may be added as long as the term 'only' is not used. The singular forms may be interpreted as the plural forms unless explicitly stated.

The elements may be interpreted to include an error margin even if not explicitly stated.

When the position relation between two parts is described using the terms 'on', 'over', 'under', 'next to' and the like, one or more parts may be positioned between the two parts as long as the term 'immediately' or 'directly' is not used.

When the temporal relationship between two events is described using the terms 'after', 'following', 'next', 'before' and the like, the two events may not occur in succession as long as the term 'immediately' or 'directly' is not used.

It will be understood that, although the terms first, second, etc., may be used to describe various elements, these elements should not be limited by these terms. These terms are only used to distinguish one element from another element. Thus, a first element discussed below could be termed a second element without departing from the technical spirit of the present invention.

The features of various exemplary embodiments of the present invention may be combined with one another either partly or wholly, and may technically interact or work together in various ways. The exemplary embodiments may be carried out independently or in combination with one another.

Hereinafter, various exemplary embodiments of the present invention will be described in detail with reference to the accompanying drawings.

FIG. 1 is a view showing an organic light emitting display device according to an example embodiment of the present invention.

Referring to FIG. 1, an organic light emitting display device 100 according to an exemplary embodiment of the present invention comprises organic layers 120, 130, 135, 140, 145, 150, and 160 between an anode 110 and a cathode 170. The anode 110 is a hole injection electrode, and may be formed of ITO (indium tin oxide), IZO (indium zinc oxide), or ZnO (zinc oxide) having a high work function. Also, if the anode 110 is a reflective electrode, the anode 110 may further comprise a reflective layer formed of aluminum (Al), silver (Ag), or nickel (Ni) under a layer formed of ITO, IZO, or ZnO.

A hole injection layer 120 is over the anode 110. The hole injection layer 120 may function to facilitate hole injection from the anode 110 to a light emitting layer 140, and may be formed of, but not limited to, one among CuPc (copper phthalocyanine), PEDOT (poly(3,4)-ethylenedioxythiophene), PANI (polyaniline), and NPD ((N,N'-bis(naphthalene-1-yl)-N,N'-bis(phenyl)-2,2'-dimethylbenzidine). The hole injection layer 120 may be 1 to 150 nm thickness. If the hole injection layer 120 is 1 nm thickness or greater, the hole injection properties may be improved, or if the hole injection layer 120 is 150 nm thickness or less, an increase in the thickness of the hole injection layer 120 may be prevented and a rise in operating voltage may be therefore prevented. The hole injection layer 120 may not be included in the composition of the organic light emitting display device, depending on the structure or characteristics of the device.

A hole transport layer 130 is over the hole injection layer 120. The hole transport layer 130 may function to facilitate hole transport, and may be formed of, but not limited to, one among NPD (N,N'-bis(naphthalene-1-yl)-N,N'-bis(phenyl)-2,2'-dimethylbenzidine), TPD (N,N'-bis-(3-methylphenyl)-N,N'-bis(phenyl)-benzidine), spiro-TAD (2,2'7,7'-tetrakis (N,N-diphenylamino)-9,9'-spirofluorene), and MTDATA (4,4',4"-Tris(N-3-methylphenyl-N-phenylamino)-triphenylamine). The hole transport layer 130 may be 1 to 150 nm thickness. If the hole transport layer 130 is 1 nm thickness or greater, the hole transport properties may be improved, or if the hole transport layer 130 is 150 nm thickness or less, an increase in the thickness of the hole transport layer 130 may be prevented, and a rise in operating voltage may be therefore prevented.

An electron blocking layer 135 is over the hole transport layer 130. The electron blocking layer 135 functions to block electrons injected from the cathode 170 to the anode 110, and may be formed of, but not limited to, one among TPD (N,N'-bis-(3-methylphenyl)-N,N'-bis(phenyl)-benzidine), NPD (N,N'-bis(naphthalene-1-yl)-N,N'-bis(phenyl)-2,2'-dimethylbenzidine), TCTA (4,4'4"-tris)carbozoyl-9-yl) triphenylamine), and CBP (4,4'-bis(carbazol-9-yl)biphenyl. The electron blocking layer 135 may not be included in the composition of the organic light emitting display device, depending on the structure or characteristics of the device.

The light emitting layer 140 is over the electron blocking layer 135. The light emitting layer 140 may emit light of red (R), green (G), and blue (B), and may be formed of a phosphorescent material. The light emitting layer 140 comprises a host and a dopant. The host serves to transfer energy to the dopant. Thus, the present inventors used an indolocarbazole compound as the host, in order to improve the properties of the light emitting layer 140. The indolocarbazole compound has carbazole with hole transfer properties and heteroaryl with electron transfer properties. The indolocarbazole compound has bipolarity involving the properties of both holes and electrons, and therefore has electric stability against holes and electrons. In the present invention, the use of an indolocarbazole compound with electric stability against holes and electrons as a host for the light emitting layer can increase the light emission area of the light emitting layer and therefore improve the lifetime of the device. Also, a host material with an indolocarbazole compound bound to a compound having an aryl group or heteroaryl group may be used for the light emitting layer to optimize the lifetime and efficiency of an organic emissive layer. Moreover, the indolocarbazole compound is capable of improving the efficiency and lifetime of the device because carbazole having a rigid structure by connecting bridge carbazole allows the energy of the host by thermal energy to be consumed only for light emission but not for other things. In addition, a compound formed by linking a carbazole derivative and a carbazole compound to an aryl group or heteroaryl group can improve the efficiency and lifetime of the device. Further, an indolocarbazole compound having carbazole and heteroaryl has high triplet energy and achieves thermal stability. Also, the use of an indolocarbazole compound as at least one among the hole transport layer, the electron blocking layer, the hole blocking layer, and the electron transport layer can facilitate hole or electron injection into the light emitting layer, thereby improving the lifetime of the device.

Accordingly, a host for the light emitting layer 140 of the present invention includes an indolocarbazole compound represented by the following Chemical Formula 1. The host has carbazole and heteroaryl.

[Chemical Formula 1]

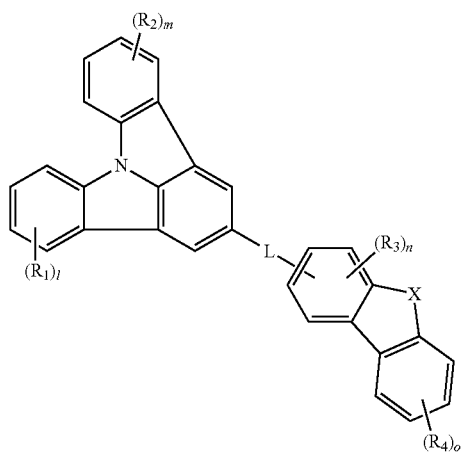

where X is one among N, O, S, and Se, wherein N is bound to one among H, a halogen atom, a cyano group, a substituted or unsubstituted alkyl group having 1 to 20 carbon atoms, a substituted or unsubstituted aryl group having 6 to 30 carbon atoms, a substituted or unsubstituted heteroaryl group having 2 to 30 carbon atoms, a substituted or unsubstituted aryl amino group having 6 to 30 carbon atoms, and a substituted or unsubstituted heteroaryl amino group having 2 to 30 carbon atoms, $R_1$ to $R_4$ are independently one among H, a halogen atom, a cyano group, a substituted or unsubstituted alkyl group having 1 to 20 carbon atoms, a substituted or unsubstituted aryl group having 6 to 30 carbon atoms, a substituted or unsubstituted heteroaryl group having 2 to 30 carbon atoms, a substituted or unsubstituted aryl amino group having 6 to 30 carbon atoms, and a substituted or unsubstituted heteroaryl amino group having 2 to 30 carbon atoms, l, m, n, and o are an integer between 0 and 4, wherein, if any of l, m, n, and o has a value of 2 or more, the corresponding R is the same with each other or if any of l, m, n, and o has a value of 2 or more, the corresponding R is different from each other, and L is a substituted or unsubstituted aryl group having 6 to 30 carbon atoms or a substituted or unsubstituted heteroaryl group having 2 to 30 carbon atoms.

The indolocarbazole compound is one among the following compounds:

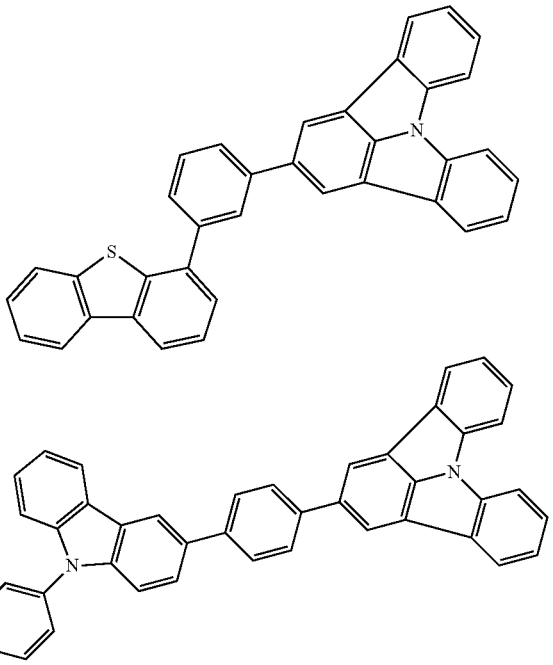

If the light emitting layer 140 is a red emitting layer, it may be formed of, but not limited to, a phosphorescent material having a host material such as CBP (4,4'-bis(carbazole-9-yl)biphenyl) and a dopant having one or more among Ir(PIQ)$_2$(acac)(bis(1-phenylisoquinoline)acetylacetonate iridium(III)), Ir(PIQ)$_3$(tris(1-phenylquinoline) iridium(III)) 및 PtOEP (octaethylporphine platinum). If the light emitting layer 140 is a green emitting layer, it may be formed of, but not limited to, a phosphorescent material having a host material such as CBP (4,4'-bis(carbazole-9-yl)biphenyl) and a dopant material comprising an iridium-based material. Alternatively, the light emitting layer 140 may be formed of, but not limited to, a fluorescent material comprising Alq$_3$(tris(8-hydroxyquinolinato)aluminum). If the light emitting layer 140 is a blue emitting layer, it may be formed of, but not limited to, a phosphorescent material having a host material such as CBP (4,4'-bis(carbazole-9-yl)biphenyl) and a dopant material comprising an iridium-based material. Alternatively, the light emitting layer 140 may be formed of, but not limited to, a fluorescent material having any one among spiro-DPVBi, spiro-CBP, distyrylbenzene (DSB), distyrylarylene (DSA), a PFO polymer, and a PPV polymer.

A hole blocking layer 145 is over the light emitting layer 140. The hole blocking layer 145 functions to block holes injected from the anode 110 from moving to the cathode 170, and may be formed of, but not limited to, one among BAlq (Bis(2-methyl-8-quinolinolate)-4-(phenylphenolato) aluminum), BCP (2,9-dimethyl-4,7-diphenyl-1,10-phenanthroline), and TPBI (2,2'2"-(1,3,5-benzinetriyl)-tris(1-phenyl-1-H-benzimidazole). The hole blocking layer 145 is 10 to 100 Å thickness. This is because, if the hole blocking layer 145 is less than 10 Å thickness, it has poor hole blocking properties, or if the hole blocking layer 145 is more than 100 Å thickness, the operating voltage of the device may rise. The hole blocking layer 145 may not be included in the composition of the organic light emitting display device, depending on the structure or characteristics of the device.

An electron transport layer 150 is over the hole blocking layer 145. The electron transport layer 150 functions to facilitate electron transport, and may be formed of, but not limited to, one among Alq3(tris(8-hydroxyquinolinato)aluminum), PBD (2-(4-biphenyl)-5-(4-tert-butylphenyl)-1,3,4-oxadiazole), TAZ (3-(4-biphenyl)-4-phenyl-5-tert-butylphenyl-1,2,4-triazole), and BAlq (Bis(2-methyl-8-quinolinolate)-4-(phenylphenolato)aluminum). The electron transport layer 150 may be 1 to 150 nm thickness. If the electron transport layer 150 is 1 nm thickness or greater, a degradation of the electron transport properties may be prevented, or if the electron transport layer 150 is 150 nm thickness or less, an increase in the thickness of the electron transport layer 150 may be prevented, and a rise in operating voltage may be therefore prevented.

An electron injection layer 160 is over the electron transport layer 150. The electron injection layer 160 functions to facilitate electron injection, and may be formed of, but not limited to, one among Alq3 (tris(8-hydroxyquinolinato)aluminum), PBD (2-4-biphenyl)-5-(4-tert-butylphenyl)-1,3,4-oxadiazole), TAZ (3-(4-biphenyl)-4-phenyl-5-tert-butylphenyl-1,2,4-triazole), or BAlq (Bis(2-methyl-8-quinolinolate)-4-(phenylphenolato)aluminum). On the other hand, the electron injection layer 160 may be formed of a metal compound, and the metal compound may be, for example, but not limited to, one among LiQ, LiF, NaF, KF, RbF, CsF, FrF, $BeF_2$, $MgF_2$, $CaF_2$, $SrF_2$, $BaF_2$, and $RaF_2$. The electron injection layer 160 may be 1 to 50 nm thickness. If the electron injection layer 160 is 1 nm thickness or greater, a degradation of the electron injection properties may be prevented, or if the electron injection layer 160 is 50 nm thickness or less, an increase in the thickness of the electron injection layer 160 may be prevented, and a rise in operating voltage may be therefore prevented.

The cathode 170 is an electron injection electrode, and may be formed of magnesium (Mg), calcium (Ca), aluminum (Al), silver (Ag), or an alloy thereof, having a low work function. If the organic light emitting display device is a top-emission type or a dual-emission type, the cathode 170 may be formed thin enough to pass light therethrough. If the organic light emitting display device is a bottom-emission type, the cathode 170 may be formed thickness enough to reflect light.

As stated above, in the present invention, the use of an indolocarbazole compound with electric stability against holes and electrons as a host for the light emitting layer can increase the light emission area of the light emitting layer and therefore improve the lifetime of the device. Also, a host material with an indolocarbazole compound bound to a compound having an aryl group or heteroaryl group may be used for the light emitting layer to optimize the lifetime and efficiency of an organic light emitting display device. Moreover, the indolocarbazole compound is capable of improving the efficiency and lifetime of the device because carbazole having a rigid structure by connecting bridge carbazole allows the energy of thermal motion of the host to be consumed only for light emission but not for other things. In addition, a compound formed by linking a carbazole derivative and a carbazole compound to an aryl group or heteroaryl group can improve the efficiency and lifetime of the device. Further, an indolocarbazole compound having carbazole and heteroaryl has high triplet energy and achieves thermal stability.

Hereinafter, synthesis examples of indolocarbazole compounds of the present invention and the properties of these compounds will be described in detail. However, the following examples are only for illustration, and the present invention is not limited thereto.

1) Synthesis of Compound A

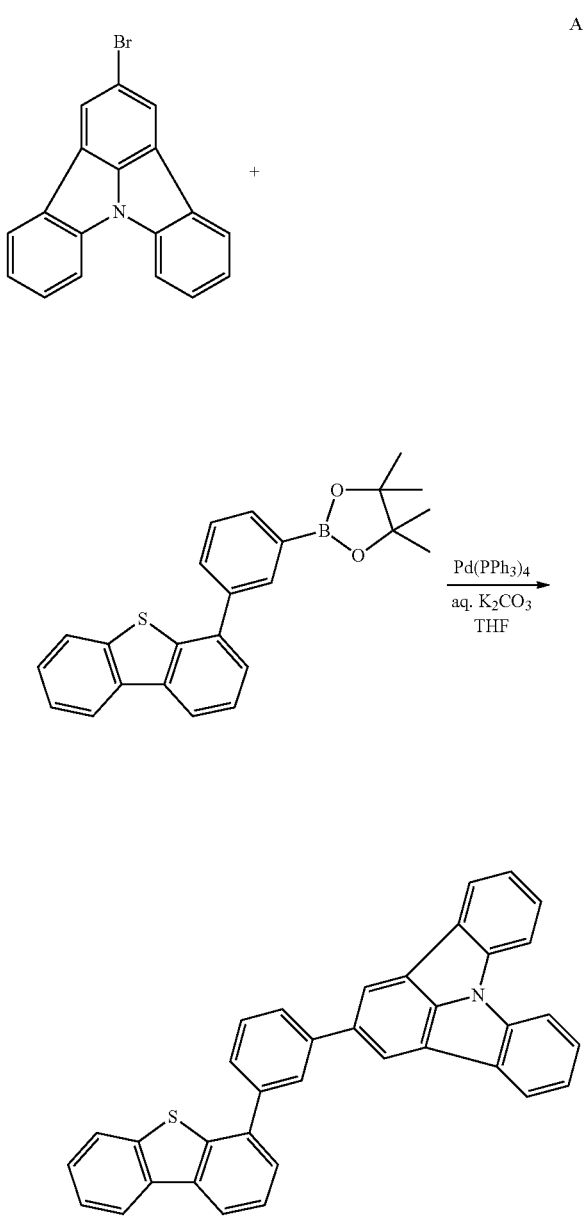

2-bromoindolo[3,2,1-jk]carbazole (6.0 g, 18.7 mmol), 2-(3-(dibenzo[b,d]thiophen-4-yl)phenyl)-4,4,5,5-tetramethyl-1,3,2-dioxaborolane) (8.7 g, 22.5 mmol), Tetrakis(triphenylphosphine)palladium(0) (Pd(pph$_3$)$_4$) (0.64 g, 0.55 mmol), 50 mL of 2M potassium carbonate ($K_2CO_3$) aqueous solution, 120 mL of tetrahydrofuran (THF) were put into a 250 mL round bottom flask under an argon atmosphere and then refluxed and stirred. After confirming completion of the reaction through thin-layer chromatography (TLC), organic layers were separated from the reaction solution, distilled under reduced pressure, and then subjected to column chromatography, thereby obtaining Compound A.

2) Synthesis of Compound B

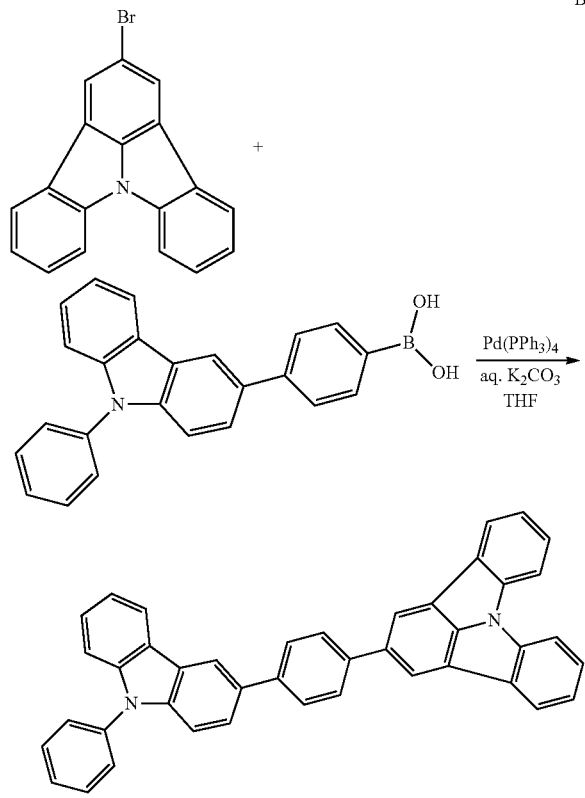

2-bromoindolo[3,2,1-jk]carbazole (6.0 g, 18.7 mmol), 4-(9-phenyl-9H-carbazole-3-yl)phenylboronic acid) (8.2 g, 22.5 mmol, Tetrakis(triphenylphosphine)palladium(0) (Pd (pph$_3$)$_4$) (0.64 g, 0.55 mmol), 50 mL of 2M potassium carbonate (K$_2$CO$_3$) aqueous solution, 120 mL of tetrahydrofuran (THF) were put into a 250 mL round bottom flask under an argon atmosphere and then refluxed and stirred. After confirming completion of the reaction through thin-layer chromatography (TLC), organic layers were separated from the reaction solution, distilled under reduced pressure, and then subjected to column chromatography, thereby obtaining Compound B.

Figure 2:
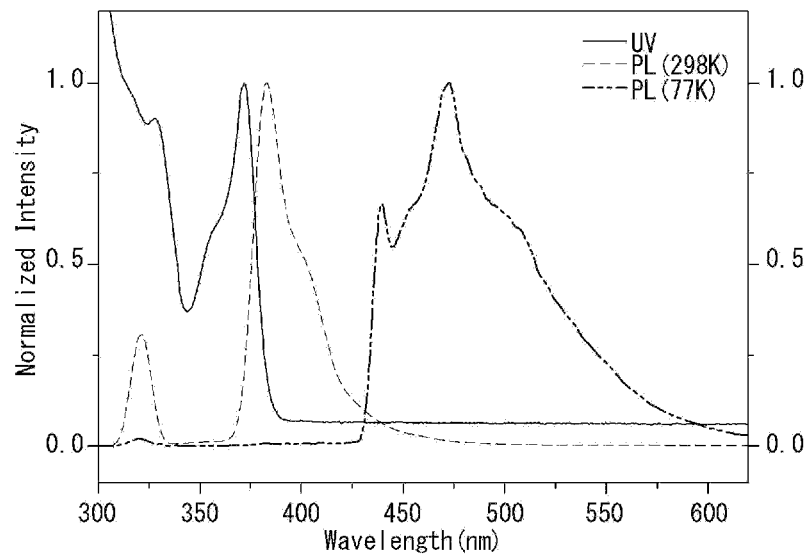
FIG. 2 is a graph showing the UV absorption spectrum, PL spectrum, and low-temperature (−77K) PL spectrum of Compound A according to an example of the present invention.
Figure 3:
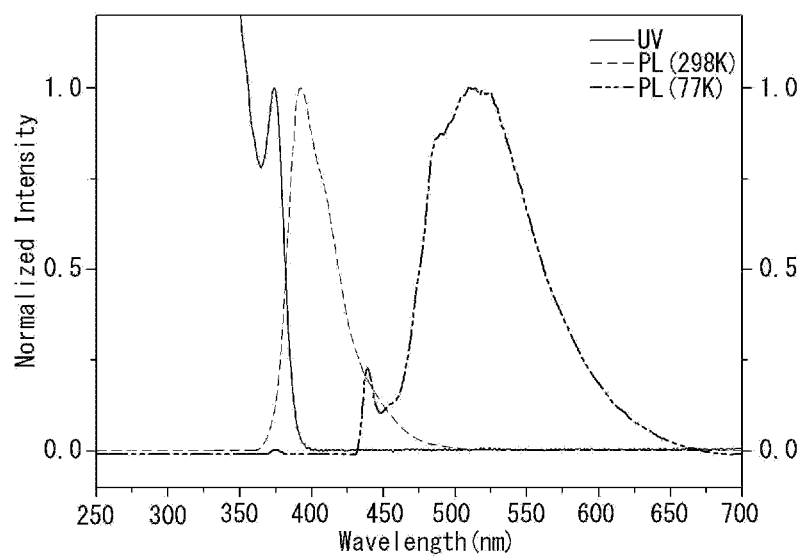
FIG. 3 is a graph showing the UV absorption spectrum, PL spectrum, and low-temperature (−77K) PL spectrum of Compound B according to an example of the present invention.

The UV absorption spectrum, PL spectrum, and low-temperature (−77K) PL spectrum of Compound A and Compound B were measured and shown in FIGS. 2 and 3, respectively. A UV spectrum refers to the absorption spectrum of a material irradiated with light in the UV region, a PL spectrum refers to the spectrum of a material produced when an excited electron drops to the ground state, and a low-temperature PL spectrum refers to the PL spectrum of a material at a low temperature, in which the first peak in a longer wavelength region than in the room-temperature PL spectrum represents the triplet energy. In FIGS. 2 and 3, the maximum intensity of light in the UV absorption spectrum was set to 1.0, and the PL and low-temperature PL spectrum measurements were shown to be proportional to the UV absorption spectrum measurements.

Referring to FIG. 2, Compound A showed a wavelength of 370 nm at the peak value of the UV absorption spectrum, a wavelength of 380 nm at the peak value of the PL spectrum, and a wavelength of 475 nm at the peak value of the low-temperature PL spectrum. Also, it was found out from the low-temperature PL spectrum that the triplet energy was 2.8 eV, which means that Compound A of the present invention is suitable as a host.

Referring to FIG. 3, Compound B showed a wavelength of 374 nm at the peak value of the UV absorption spectrum, a wavelength of 385 nm at the peak value of the PL spectrum, and a wavelength of 512 nm at the peak value of the low-temperature PL spectrum. Also, it was found out from the low-temperature PL spectrum that the triplet energy was 2.8 eV, which means that Compound B of the present invention is suitable as a host.

Hereinafter, an embodiment for the manufacture of an organic light emitting display device according to the present invention will be disclosed. However, the following materials for the electron transport layer do not limit the scope of the present invention.

Comparative Example

An organic light emitting display device comprising a hole injection layer, a hole transport layer, an electron blocking layer, a light emitting layer, a hole blocking layer, an electron transport layer, an electron injection layer, and a cathode was formed on a substrate. The light emitting layer was a green light emitting layer which comprises CBP as a host and Ir(ppy)$_3$ (tris(2-phenylpyridine)iridium(III)) with a 15% doping concentration. The device used in testing was a mono device.

Embodiment 1

The organic light emitting display device has the same composition as Comparative Example, and the light emitting layer is a green light emitting layer which comprises Compound A as a host and Ir(ppy)$_3$ (tris(2-phenylpyridine) iridium(III)) as a dopant with a 15% doping concentration.

Embodiment 2

The organic light emitting display device has the same composition as Comparative Example, and the light emitting layer is a green light emitting layer which comprises Compound B as a host and Ir(ppy)$_3$ (tris(2-phenylpyridine) iridium(III)) as a dopant with a 15% doping concentration.

The materials for the light emitting layer used in the above Comparative Example and Embodiments 1 and 2 do not limit the scope of the present invention.

The operating voltage, current density, external quantum efficiency, and lifetime of the devices manufactured according to Comparative Example and Embodiments 1 and 2 were measured and shown in the following Table 1 (Hereinbelow, the operating voltage, external quantum efficiency, and lifetime measurements taken in the embodiments were expressed as a percentage relative to those taken in Comparative Example corresponding to 100%.)

TABLE 1

| | Operating voltage (%) | Current density (mA/cm$^2$) | External quantum efficiency (%) | Lifetime (%) |
|---|---|---|---|---|
| Comparative Example | 100 | 10 | 100 | 100 |
| Embodiment 1 | 92 | 10 | 116 | 451 |

TABLE 1-continued

| | Operating voltage (%) | Current density (mA/cm²) | External quantum efficiency (%) | Lifetime (%) |
|---|---|---|---|---|
| Embodiment 2 | 92 | 10 | 108 | 528 |

Referring to Table 1, Embodiment 1 using the indolocarbazole compound A as a host showed an 8% decrease in operating voltage and a 16% increase in external quantum efficiency, compared to Comparative Example using CBP as a host. Also, Embodiment 1 showed a 351% increase in lifetime, compared to Comparative Example. Embodiment 2 using the indolocarbazole compound B as a host showed an 8% decrease in operating voltage and an 8% increase in external quantum efficiency, compared to Comparative Example. Also, Embodiment 2 showed a 428% increase in lifetime, compared to Comparative Example.

As stated above, in the present invention, the use of an indolocarbazole compound with electric stability against holes and electrons as a host for the light emitting layer can increase the light emission area of the light emitting layer and therefore improve the lifetime of the device. Also, a host material with an indolocarbazole compound bound to a compound having an aryl group or heteroaryl group may be used for the light emitting layer to optimize the lifetime and the efficiency of an organic emissive layer. Moreover, the indolocarbazole compound is capable of improving the efficiency and the lifetime of the device because carbazole having a rigid structure by connecting bridge carbazole allows the energy of the host by thermal energy to be consumed only for light emission but not for other things. In addition, a compound formed by linking a carbazole derivative and a carbazole compound to an aryl group or heteroaryl group can improve the efficiency and lifetime of the device. Further, an indolocarbazole compound having carbazole and heteroaryl has high triplet energy and achieves thermal stability.

It will be apparent to those skilled in the art that various modifications and variations can be made in the organic light emitting display device of the present invention without departing from the spirit or scope of the invention. Thus, it is intended that the present invention cover the modifications and variations of this invention provided they come within the scope of the appended claims and their equivalents.

What is claimed is:

1. An organic light emitting display device comprising:
   an anode;
   an organic layer over the anode; and
   a cathode over the organic layer,
wherein the organic layer includes an indolocarbazole compound represented by the following Formula 1:

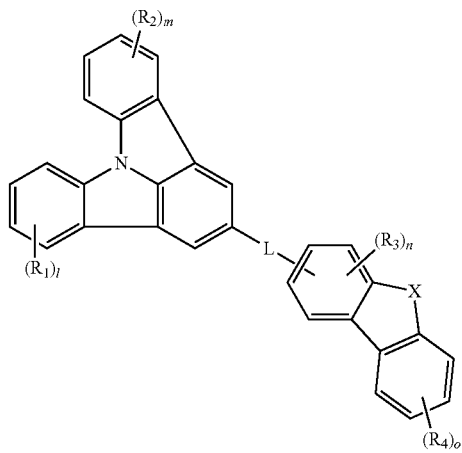

Formula 1 wherein:
   X is one among N, O, S, and Se, wherein N is bound to one among H, a halogen atom, a cyano group, a substituted or unsubstituted alkyl group having 1 to 20 carbon atoms, a substituted or unsubstituted aryl group having 6 to 30 carbon atoms, a substituted or unsubstituted heteroaryl group having 2 to 30 carbon atoms, a substituted or unsubstituted aryl amino group having 6 to 30 carbon atoms, and a substituted or unsubstituted heteroaryl amino group having 2 to 30 carbon atoms,
   $R_1$ to $R_4$ are independently one among H, a halogen atom, a cyano group, a substituted or unsubstituted alkyl group having 1 to 20 carbon atoms, a substituted or unsubstituted aryl group having 6 to 30 carbon atoms, a substituted or unsubstituted heteroaryl group having 2 to 30 carbon atoms, a substituted or unsubstituted aryl amino group having 6 to 30 carbon atoms, and a substituted or unsubstituted heteroaryl amino group having 2 to 30 carbon atoms,
   l, m, n, and o are an integer between 0 and 4, wherein, if any of l, m, n, and o has a value of 2 or more, the corresponding R is the same with each other or if any of l, m, n, and o has a value of 2 or more, the corresponding R is different from each other, and
   L is a substituted or unsubstituted phenyl group.

2. The organic light emitting display device of claim 1, wherein the indolocarbazole compound of Formula 1 includes one among the following compounds:

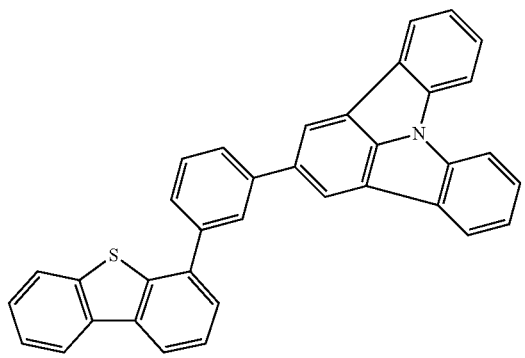

-continued

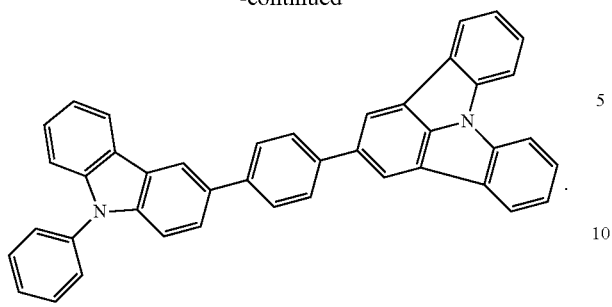

3. The organic light emitting display device of claim 1, wherein the organic layer includes a light emitting layer.

4. The organic light emitting display device of claim 3, wherein the light emitting layer includes the indolocarbazole compound of Formula 1.

5. The organic light emitting display device of claim 1, wherein the organic layer includes at least one among a hole transport layer, an electron blocking layer, a hole blocking layer, and an electron transport layer, and at least one among the hole transport layer, the electron blocking layer, the hole blocking layer, and the electron transport layer includes the indolocarbazole compound of Formula 1.

6. The organic light emitting display device of claim 1, wherein L is a substituted phenyl group.

7. The organic light emitting display device of claim 1, wherein L is an unsubstituted phenyl group.

* * * * *